May 29, 1973 W. A. WARRINER Plant Pat. 3,347
ROSE PLANT
Filed Sept. 10, 1971
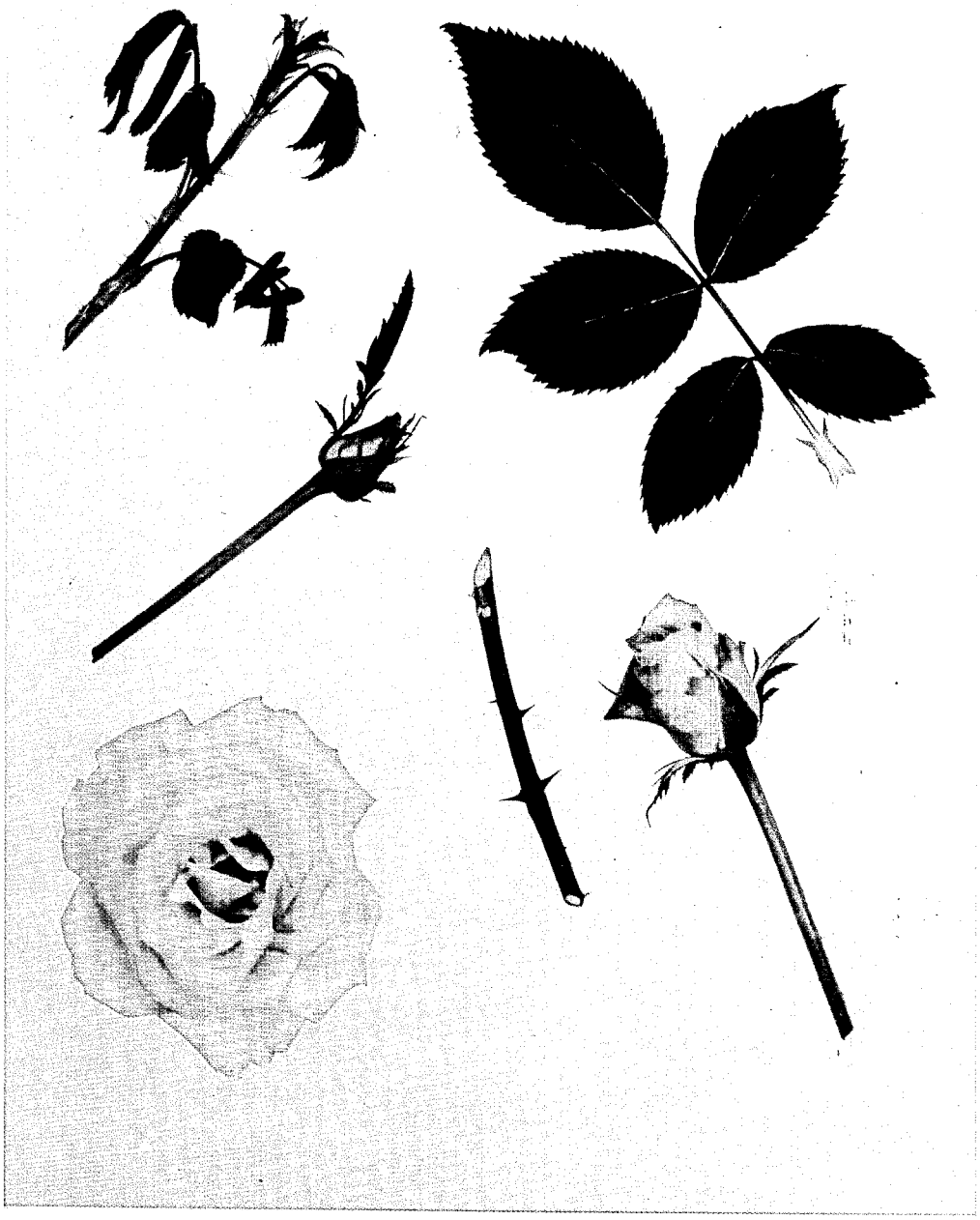
WILLIAM A. WARRINER
INVENTOR
BY
BUCKHORN, BLORE, KLARQUIST & SPARKMAN
ATTORNEYS

United States Patent Office

Plant Pat. 3,347
Patented May 29, 1973

3,347
ROSE PLANT

William A. Warriner, Tustin, Calif., assignor to Jackson & Perkins Co., Medford, Oreg.

Filed Sept. 10, 1971, Ser. No. 179,599
Int. Cl. A01h *5/00*
U.S. Cl. Plt.—28 1 Claim

This present invention relates to a new and distinct variety of rose plant of the floribunda class, which was originated by me by crossing an unnamed variety with the variety Ginger, U.S. Plant Patent 2,293.

The primary objective of this breeding was to produce a new and improved floribunda rose suitable for use as a garden variety and as a greenhouse cut flower variety and to be particularly resistant to powdery mildew disease (*Spaerotheca pannosa rosae*). This objective was fully achieved, along with other desirable features, as evidenced by the following unique combination of characteristics which are outstanding in the new variety and which distinguish it from its parents as well as from all other variety Ginger, U.S. Plant Patent 2,293.

(1) An unusually vigorous habit of growth under greenhouse conditions.

(2) A unique color of a brilliant Vermilion.

(3) Good keeping quality as a cut flower with unusually stiff and thick petals.

(4) A very small receptacle which appears as only a slight swelling of the stem under the flower.

(5) A resistance to rose powdery mildew (*Spaerotheca pannosa rosae*) such that this disease is rarely present on this new variety.

Asexual reproduction of my new variety by budding as performed at Wasco, Calif. shows that the aforementioned characteristics and distinctions come true to form and are established and transmitted through succeeding propagations.

The accompanying drawing shows typical specimens of the vegetative growth and flowers of the new variety in different stages of development, and as depicted in color as nearly true as it is reasonably possible to make the same in a color illustration of this character.

The following is a detailed description of the new rose variety, with color terminology in accordance with Wilson's Horticultural Color Chart, except where a general color term of ordinary dictionary significance is indicated.

Percentage: Seedling.
- *Seed parent.*—An unnamed variety.
- *Pollen parents.*—Ginger.

Classification:
- *Botanic.*—Rosa hybrid.
- *Commercial.*—Floribunda.

*Flower*

Observations were made in June in the morning at Irvine, Calif. of plants grown in a greenhouse.

Blooming habit: Recurrent—continuous.

Bud:
- *Size.*—1" when petals start to unfurl.
- *Form.*—Pointed, ovoid.
- *Color.*—When sepals first divide—near Blood Red (820). When half blown—inside of petals—Vermilion (18), uniform color over all of petal except small nearly white area at base of petal; reverse of petals—Signal Red (719/3), white area at base of petal is not sharply defined.
- *Sepals.*—Color: outside—Spinach Green (0960/3), lighter at base. Inside—lighter than Spinach Green and covered with tomentum; very light at base of sepal. Three appendaged sepals lightly appendaged. Two unappendaged sepals hairy edged.
- *Receptacle.*—Color: slightly lighter than Spinach Green (0960/3). Shape: only a slight enlargement of peduncle at base of flower. Size: small. Surface: smooth.
- *Peduncle.*—Length: medium. Surface: prickly. Color: slightly lighter than Spinach Green (0960/3). Strength: stiff, erect.
- *Opening.*—Petals undulated with very little curling or recurving.

Bloom:
- *Size.*—Medium. Average size when fully expanded 2½"–3".
- *Borne.*—Several together.
- *Stems.*—Long.
- *Form.*—When first open—high center. Permanence—retains its form to the end.
- *Petalage.*—From 15 to 20.
- *Color.*—Center of flower: upper side of petals—uniformly Dutch Vermilion (717). Reverse side of petals—uniformly Orient Red (819/3). Outer petals: upper side of petals—same as center petals. Reverse of petals—same as center petals. Base of petals—very small area of light yellow. General tonality from a distance—Dutch Vermilion (717). No variegations.
- *Discoloration.*—General tonality at end of first day—no change. Third day—upper side Scarlet (19), lower side Crimson (22).
- *Fragrance.*—None.

Petals:
- *Texture.*—Thick. Petals are very stiff.
- *Surface.*—Inside—satiny. Reverse—smooth, no gloss.
- *Shape.*—Round.
- *Form.*—Slightly undulated.
- *Arrangement.*—Imbricated.
- *Petaloids in center.*—Few, large.
- *Lastingness.*—On the plant—very long. As cut flower—very long.

Reproductive parts:
- *Anthers.*—Large. Color—Yellow. Arrangement—regular around styles.
- *Stamens, filaments (threads)*—Short. Color—white.
- *Pollen.*—Color—gold yellow.
- *Styles.*—Loosely separated, thin.
- *Stigmas.*—Color—very light yellow.
- *Ovaries.*—All enclosed in calyx.

*Plant*

Form: Bush.

Growth: Very vigorous. Side shoots must be removed from some of the stems when used as a florist cut flower.

Foliage: Usually 5, occasionally 7 leaflets.
- *Size.*—Large.
- *Quantity.*—Abundant.
- *Color.*—New foliage: Fern Green (0862/3) when very small, edged with Garnet Brown (00918/3), darkening as leaves unfold to Spinach Green (0960) overlaid with Garnet Brown. Old foliage: Slightly darker than Parsley Green (00962).

Leaflets:
- *Shape.*—Oval pointed.
- *Texture.*—Leathery on upper side. Under side—smooth. Ribs and Veins—ordinary.
- *Edge.*—Serrated, undulated.
- *Serration.*—Single, small.
- *Petiole.*—Rachis—color green. Under side—prickles.
- *Stipules.*—Long, glandular.
- *Disease resistance.*—Resistant to mildew, under normal growing conditions at Irvine, Calif.

Wood:

*New Wood.*—Color—Light green. Bark—smooth.

*Old wood.* — Color — Spinach Green (0960/2). Bark—smooth.

Thorns:

*Quantity.*—On main stalks from base—many. On laterals from stalk—many.

*Form.*—Flat base, long, straight.

*Color when young.*—Red.

*Position.*—Irregular.

Prickles:

*Quantity.*—On main stalks.—few. On laterals—few.

*Color.*—Brown.

Short needles:

*Quantity.*—On main stalks.—few. On laterals—few.

I claim:

1. A new and distinct variety of rose plant of the floribunda class, substantially as herein shown and described, characterized particularly as to novelty by the unique combination of an extremely vigorous habit of growth; excellent suitability as a cut flower because of a brilliant vermilion flower color, and unusually long vase life (often more than 7 or 8 days); and near immunity to attacks by rose powdery mildew.

No references cited.

ROBERT E. BAGWILL, Primary Examiner

)-1050
;/69)

UNITED STATES PATENT OFFICE
CERTIFICATE OF CORRECTION atent No. PP 3,347 Dated May 29, 1973 nventor(s) William A. Warriner

It is certified that error appears in the above-identified patent ınd that said Letters Patent are hereby corrected as shown below:

›lumn 1, line 21, "variety Ginger, U.S. Plant Patent 2,293" ıould read --varieties of which I am aware: --.

Signed and sealed this 22nd day of January 1974.

SEAL)
ıttest:

EDWARD M. FLETCHER, JR.
ıttesting Officer

RENE D. TEGTMEYER
Acting Commissioner of Patents